United States Patent
Shon et al.

(10) Patent No.: US 6,806,722 B2
(45) Date of Patent: Oct. 19, 2004

(54) POLYMER-TYPE HUMIDITY SENSOR

(75) Inventors: Jong-Chull Shon, Suwon (KR); Keun-Seuk Oh, Suwon (KR); So-Hyun Lee, Suwon (KR); Won-Woo Lee, Suwon (KR); Jung-Eui Hoh, Suwon (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 10/005,223

(22) Filed: Dec. 7, 2001

(65) Prior Publication Data

US 2003/0107385 A1 Jun. 12, 2003

(51) Int. Cl.[7] .............................................. G01R 27/08
(52) U.S. Cl. ...................................................... 324/694
(58) Field of Search ............................ 338/35; 324/694, 324/695, 696, 691, 700, 702, 703; 73/29.01, 73, 335.03; 62/176.1; 219/678, 707

(56) References Cited

U.S. PATENT DOCUMENTS

| | | | |
|---|---|---|---|
| 3,848,218 A | * 11/1974 | Wakabayashi et al. | ......... 338/35 |
| 4,080,564 A | 3/1978 | Nitta et al. | .................. 324/703 |
| 4,532,469 A | * 7/1985 | Wardell | ....................... 324/689 |
| 4,598,393 A | 7/1986 | Pierce et al. | |
| 5,661,405 A | * 8/1997 | Simon et al. | ................ 324/697 |
| 5,847,261 A | * 12/1998 | Lee | .............................. 73/1.07 |
| 6,375,863 B1 | * 4/2002 | Tachikawa et al. | ..... 252/299.01 |
| 6,429,265 B2 | * 8/2002 | Nishida | .................... 525/329.5 |
| 6,430,379 B1 | * 8/2002 | Takahashi et al. | ............. 399/44 |

FOREIGN PATENT DOCUMENTS

| | | |
|---|---|---|
| EP | 0 359 269 A1 | 9/1989 |
| JP | 01-266182 | 10/1989 |
| JP | 11-6809 | 1/1999 |

OTHER PUBLICATIONS

Search Report; Dated Jun. 13, 2003 EP 02253872.

* cited by examiner

Primary Examiner—Anjan Deb
Assistant Examiner—Amy He
(74) Attorney, Agent, or Firm—Staas & Halsey LLP

(57) ABSTRACT

A polymer-type humidity sensor for use in a microwave oven and which has a polymer structure which includes a rubber and a predetermined amount of carbon, and a pair of electric terminals connected to the polymer structure. The polymer-type humidity sensor of the present invention has a rapid response time, durability, excellent adherence to terminals, low hysteresis, and exhibits stability to exposures of high temperatures and high relative humidity.

26 Claims, 3 Drawing Sheets

POLYMER-TYPE HUMIDITY SENSOR

BACKGROUND OF THE INVENTION

1. Field of the Invention

The present invention relates to a humidity sensor, and more particularly, to a polymer-type humidity sensor for applications such as a microwave oven and method of manufacturing thereof.

2. Description of the Related Art

Sensors provide variety of information to microprocessors, which in turn process the information and provide useful information to the recipient. A wide variety of information is processed by computers and microprocessors and transferred to recipients/users such as humans or machines. However, sensor technology, which aims basically at sensing and detecting basic information used by such computers, is far behind computer or communication technologies because of its higher complexity. As such, sensors have become a main hindrance to functional improvement in various systems.

Humidity is a universal parameter of common environments and its control is recognized to be very important in a variety of fields, such as industries related to precision manufacturing, fiber, food, and electronics industries.

In a microwave oven, an infrared beam temperature sensor, a gas sensor or a humidity sensor is used to monitor the heating or cooking state of the food being cooked. Infrared beam temperature sensors, although having high accuracy relative to the other sensors, are expensive and may cause errors due to a type or shape of a food container. Gas sensors are less expensive than the infrared beam temperature sensors. However, gas sensors are unable to selectively sense desired gases due to the variety of gases generated according to a type of food kinds or even from a single food type. In contrast, humidity sensors are relatively inexpensive. They are also designed to detect water molecules or moisture, which are generated from all types of food upon heating, and to thus monitor the cooking state of the food. With these advantages, humidity sensors are now the most extensively used sensor in general-purpose microwave ovens.

A conventional humidity sensor utilizing a wafer of an $MgCr_2O_4$—$TiO_2$ spinnel solid-solution was first developed by Nitta et al., (U.S. Pat. No. 4,080,564). Subsequently, a ceramic-type humidity sensor was developed utilizing $TiO_2$—$V_2O_5$, $MgAl_2O_4$, $ZnCr_2O$—$LiZnVO_4$, $Al_2O_3$, etc. Afterwards, humidity sensors using polymers were reported. Recently, active research has been directed to the development of thin film or MOS capacitor humidity sensors taking advantage of CMOS technology. Ceramic or thick film type humidity sensors can be relatively simply fabricated, but they show poor reproducibility and contamination resistance, while thin film or MOS capacitor types are fabricated in complicated processes.

Organic polymer materials have been widely used in past decades by virtue of their plasticity, lightness, corrosion resistance, and electrical insulation properties. However, the applicable use of the organic polymer materials was limited due to their inherent properties, such as low hardness, wear resistance and conductivity as compared to inorganic materials. However, recent advances in irradiation of polymers have allowed physical and chemical properties of the polymers to be modified. (Chemical treatment, heating, and irradiation of X-ray, gamma ray, UV light and/or high-energy electron beams are generalized as irradiation.) In industrial and medical fields, such treatments find numerous applications, including polymer modification, surface coating, production of heat-shrinkable tubes, thermal and electrical resistant insulators, development of biomedical materials, etc.

Additionally, polymerization techniques have been developed to the extent that polymers can have electrical terminals at their opposite ends, thereby allowing the polymers to act as resistance sensors. The polarization of polymers can be achieved by implanting ions or applying strong external fields at a drying step, which is referred to as ionic modification. This technique is implemented by high-energy irradiation, which requires the application of strong electric fields (voltages). The technology of irradiating with high-energy ion beams can also improve the conductivity of polymers and is developed to the extent of being applied to waveguides in communication fields.

FIG. 1 shows the utilization of a conventional humidity sensor 4, such as a ceramic humidity sensor 4, in an environment such as a microwave oven system 10. A magnetron 2 generates high-frequency electromagnetic waves, which are radiated to cook food 3. The ceramic humidity sensor 4 senses a humidity vapor (not shown) from the food 3 during cooking, and outputs signal to a microcomputer 5, which controls the magnetron 2. Generally, the conventional ceramic humidity sensor 4 is made from a semiconductor ceramic based on $MgCrO_4$—$TiO_2$.

FIG. 1A shows the humidity vapor contacting a surface 40 of the ceramic humidity sensor 4 composed of a semiconductor ceramic based on $MgCrO_4$—$TiO_2$. A sensor resistance is reduced when moisture droplets 41 enter the ceramic humidity sensor 4 through numerous pores 42 present in the surface of the ceramic humidity sensor 4 to alter a resistance.

The detection of humidity changes using humidity sensor 4 is based on a change in the electrical resistance or capacitance of moisture-sensitive materials used in the humidity sensor 4, thus change depends on moisture absorption into or condensing on the moisture-sensitive materials. Moisture-sensitive materials for humidity sensor 4 include electrolytes, such as LiCl, metallic materials such as Se and Ge, sintered metal oxide such as $MgCr_2O_4$, $ZnCr_2O_4$, $TiO_2$, and $SnO_2$, porous metal oxide films such as $Al_2O_3$, electroconductive particle-dispersed polymeric materials such as nylon, and organic or inorganic polymeric electrolyte films.

Humidity sensor 4 made of ceramic materials can cover a wide humidity range and are excellent in thermal resistance. However, the humidity sensors undergo time-dependent changes even when being allowed to stand at room temperature because of the characteristic instability of the metal oxides used. Specifically, the sensitivity to moisture deteriorates in a relatively short time by the hydroxides formed due to the absorption of water onto the metal oxide, or by the deposits leading to a reduction in the moisture-sensitive surface area. For this reason, the humidity sensor 4 is required to be periodically heated to 400–450° C. every 20–40 minutes to recover their performance.

In addition, because the moisture sensing capacity of ceramic-based humidity sensor 4 is fundamentally based on the physical absorption of moisture into the ceramic through the pores 42, it is difficult to reduce the detection error between sensitive devices. It is also difficult to obtain reliable detection properties through the modification of the materials properties as well as the microscopic structures such as pore size, pore distribution, and porosity.

Represented by synthetic resins, nylon, etc., polymers are substances made of giant molecules formed by the union of simple molecules, called monomers. Polymer type humidity sensors are designed to quantify the change in sensor resistance or capacitance to determine the humidity. Examples of the organic polymers used in humidity sensor 4 include polyphenylacetylene, cellulose acetate, cellulose acetate butyrate, poly(4-vinylpyridine), and various copolymers. However, conventional polymeric materials used by the current humidity sensor 4 have slow response speed, large hysteresis, and short lifespan. These drawbacks are particularly aggravated upon exposure to high temperature and high relative humidity.

Unlike ceramic-based humidity sensors, humidity sensor 4 based on thin film materials, such as polymeric electrolyte membranes, utilize the properties such as hydroscopicity and ion conductivity that the moisture-sensitive materials themselves have. Therefore, the sensing characteristics are determined by the physicochemical properties of the materials rather than by the microscopic structure of the materials.

The moisture absorbed into the polymeric electrolyte membrane helps dissolve ionic substance to increase the quantity of operable ions, resulting in a great decrease in specific resistivity. A humidity sensor 4 using the polymeric electrolyte membrane utilizes the phenomenon that the quantity of the absorbed moisture is reversibly changed depending on the moisture content (humidity) of the atmosphere, resulting in a change in the ion production and therefore, electrical conductivity.

Thin film materials have reproducible sensitivity because the manufacturing conditions have little effect on the thin film materials. It is also relatively easy to make the physical properties constant from one device to another because a plurality of the humidity sensors 4 can be fabricated on the same substrate. Moreover, unlike ceramic materials, the thin film materials do not require additional high temperature for the fabrication of the humidity sensor 4. Therefore, special materials or techniques are not required for processes such as electrode formation or lead fixation. These advantages are very helpful for making the device low-priced, small and light, as well as for integrating the device into environmental circuits. However, conventional thin film type humidity sensors require complicated manufacturing and fabrication processes.

SUMMARY OF THE INVENTION

Accordingly, it is an object of the present invention to provide a polymer-type humidity sensor with a rapid response time, durability, excellent adherence to terminals, low hysteresis, and low in cost, and a method of manufacturing the polymer-type humidity sensor.

Additional objects and advantages of the invention will be set forth in part in the description which follows and, in part, will be obvious from the description, or may be learned by practice of the invention.

To achieve the above and other objects of the present invention, a polymer-type humidity sensor according to an embodiment of the present invention includes a polymer structure, which comprises a rubber and carbon and a pair of electric terminals formed to the polymer structure.

According to an aspect of the invention, the rubber is a rubber such as NBR-Acrylonitrile Butadiene Rubber.

According to another aspect of the invention, the carbon added to the polymer is in a range of 15–20%±5% by volume of the polymer structure.

According to a further aspect of the invention, the polymer-type humidity sensor has resistance in a range of range of 500 k$\Omega$–2 M$\Omega$.

According to yet another aspect of the invention, the polymer-type humidity sensor has an impedance of $2\times10^6$ $\Omega$ and $5\times10^5$ $\Omega$ at a relative humidity range of 0% and 100% and undergoes impedance change over the whole relative humidity range.

According to another embodiment of the present invention, there is provided a method of manufacturing a polymer-type humidity sensor including obtaining a resultant composition which includes a rubber and carbon, and forming a polymer structure of a predetermined shape with a pair of electric terminals formed at the polymer structure using the resultant composition.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENTS

Figure 1:
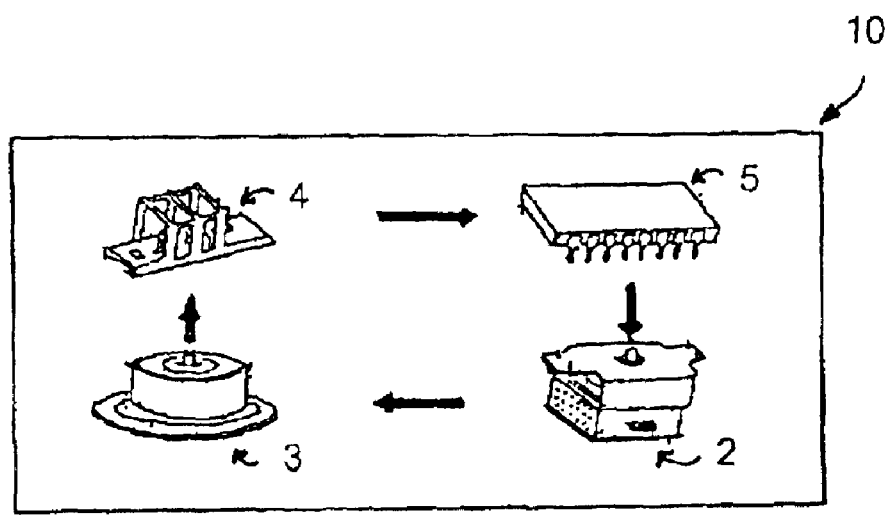
FIG. 1 is a diagram of a microwave oven system using a conventional ceramic humidity sensor.
Figure 1A:
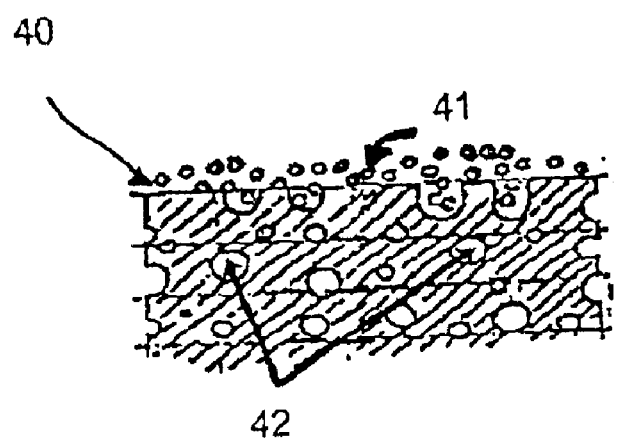
FIG. 1A is a cross-sectional view of a surface of the conventional ceramic humidity sensor showing moisture droplets entering the ceramic humidity sensor through pores.

Reference will now be made in detail to preferred embodiments of the present invention, examples of which are illustrated in the accompanying drawings, wherein like reference numerals refer to the like elements throughout. The embodiments are described below in order to explain the present invention by referring to the figures.

Figure 2:
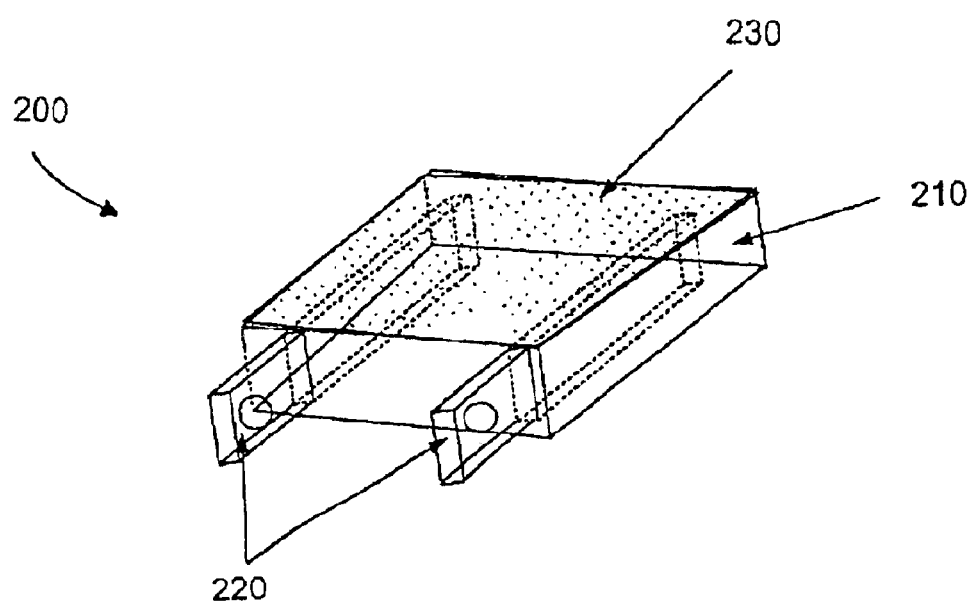
FIG. 2 is a perspective view showing an embodiment of a polymer-type humidity sensor according to an embodiment of the present invention.

FIG. 2 shows a diagram of a polymer-type humidity sensor 200 according to an embodiment of the present invention. The polymer-type humidity sensor 200 has electrical terminals 220 located to a predetermined area of the polymer 210. The electrical terminals 220 are spaced apart from each other and are buried within the polymer 210. A surface of the polymer 210, such as a moisture contacting face 230, provides a sensing area for moisture contacting the surface. The polymer 210 and the electrical electrodes 220 of the polymer-type humidity sensor 200 can have a variety of predetermined shapes and placement according to the need of the applicable system.

Figure 3:
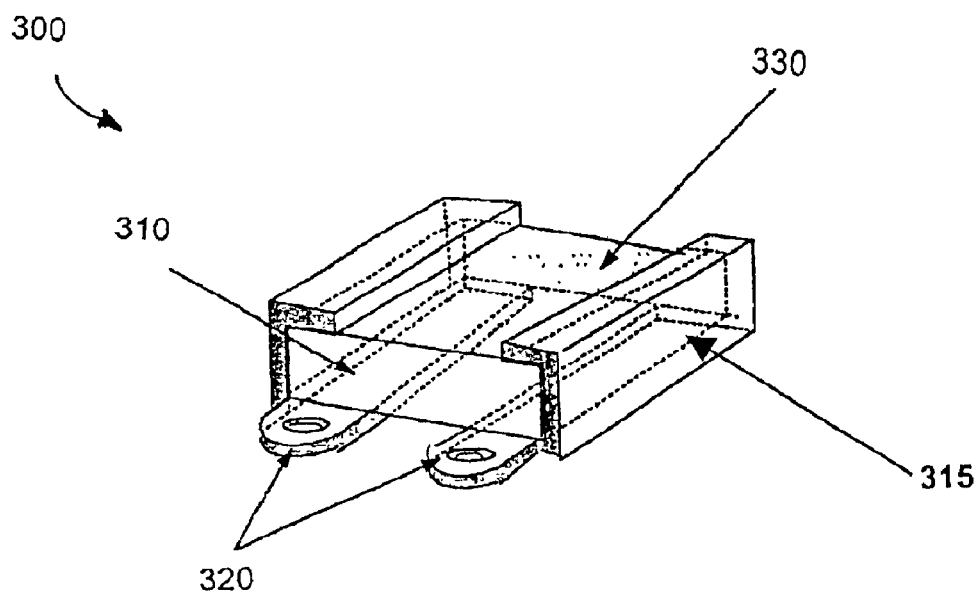
FIG. 3 is a perspective view showing a polymer-type humidity sensor according to another embodiment of the present invention.

FIG. 3 shows a diagram of another polymer-type humidity sensor 300 according to another embodiment of the present invention. The polymer-type humidity sensor 300 has external electrical terminals 320 of a predetermined shape formed on corresponding brackets 315 disposed at opposite ends of the polymer 310. A surface of the polymer 310, such as a moisture contacting face 330, provides a sensing area for moisture contacting the surface. It is understood that the external electrical terminal 320 and the bracket 315 can be a single piece as shown or can be formed separately by attaching the external electrical terminal 320 to the bracket 315.

Figure 4:
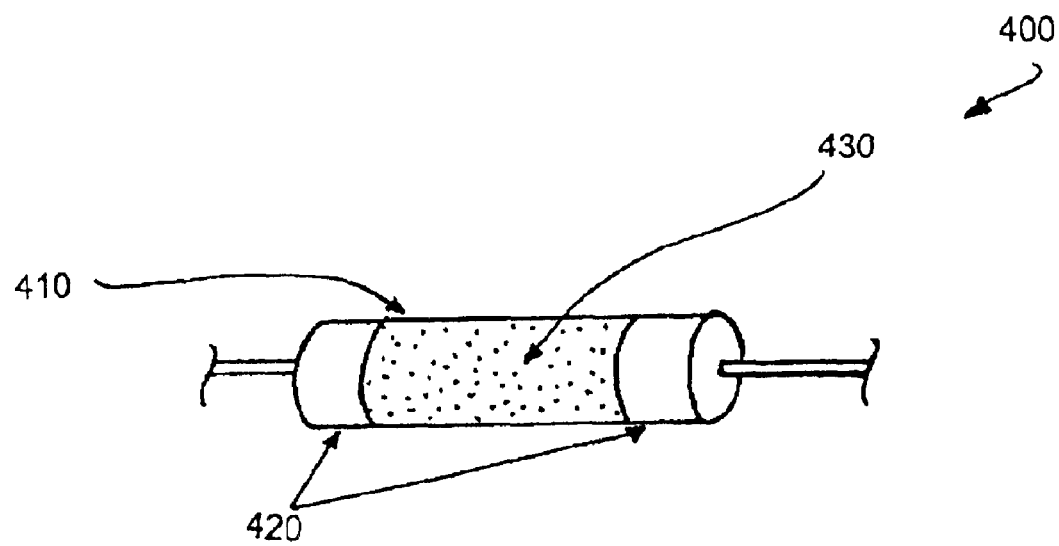
FIG. 4 is a perspective view showing a polymer-type humidity sensor according to yet another embodiment of the present invention.

FIG. 4 shows a diagram of yet another polymer-type humidity sensor 400 according to another embodiment of the present invention. A polymer 410 of the polymer-type humidity sensor 400 has a cylindrical shape with electrical terminals 420 formed to opposite ends of the polymer 410. A cylindrical contacting surface of the polymer 410 provides a moisture contacting face 430 for sensing moisture contacting the surface.

Figure 5:
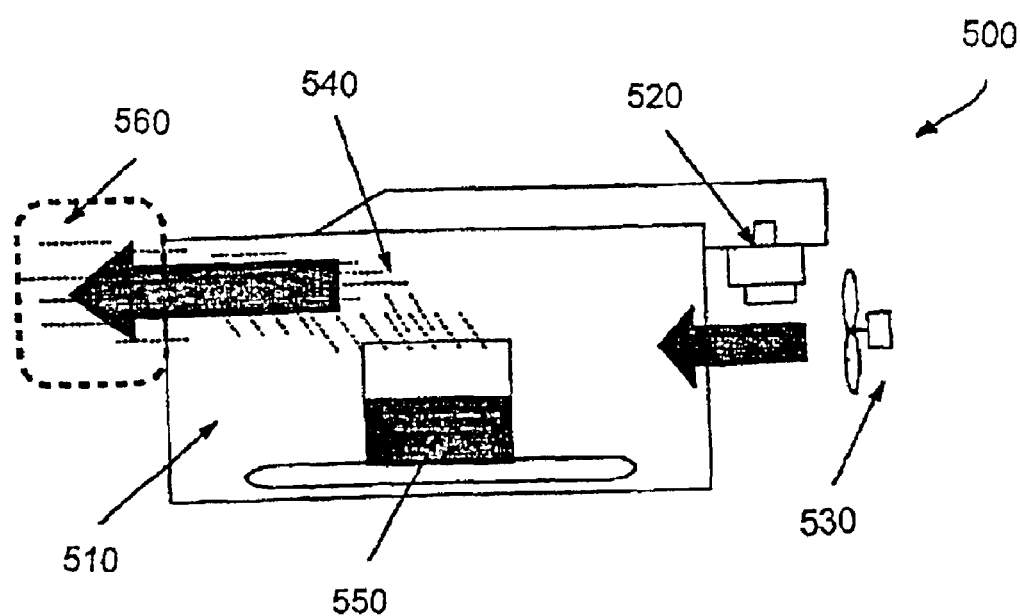
FIG. 5 is a diagram of a microwave oven system using the polymer-type humidity sensor according to an embodiment of the present invention.

FIGS. 2 and 5 show a diagram of a typical microwave oven system 500 using the polymer-type humidity sensor 200 according to present invention. The microwave oven system 500 comprises a food cavity 510, a magnetron 520 and a cooling fan 530. FIG. 5 further shows that moisture 540 generated from food 550 is directed by the cooling fan 530 towards a sensor location 560 of the polymer-type humidity sensor 200. Upon heating of the food 550, the polymer-type humidity sensor 200 located in the sensor location 560 detects moisture 540. A microcomputer (not shown) connected to the polymer-type humidity sensor 200 detects the change in resistance of the polymer-type humidity sensor 200, calculates the remaining heating time of the food 550, and automatically stops the operation of the microwave oven system 500. However, it is understood that the sensor location 560 need not be opposite the cooling fan 530 but can be located in other areas, such as adjacent the cooling fan 530 or on other walls through which portions of the moisture 540 is exhausted from the food cavity 510.

In one embodiment, a polymer-type humidity sensor according to present invention has impedances of about $2 \times 10^6$ Ω and $5 \times 10^5$ Ω at 0% and 100% relative humidity (RH), respectively and undergoes impedance changes over the whole humidity range. Also, the difference between moisture sensitivities during a moisture absorbing process (0% RH→100% RH) and a moisture desorbing process (100% RH→0% RH) is as small as 2% RH or less.

Using the polarization of ions ($H^+$), the polymer-type humidity sensor responds to moisture changes over the whole humidity range and represents the response as a resistance change. In addition, the polymer-type humidity sensor is easily fabricated and minimized in its size, so that it is advantageous in terms of production at low cost and integration into appliances.

A polymer of the present invention used in the polymer-type humidity sensor is fabricated by utilizing the cross-linking reaction of hydrophilic polymeric materials with hydrophobic polymeric materials. More specifically, the polymer of the present invention is prepared from a rubber or a natural rubber compound that is improved in electrical conductivity. The specific formulation is characterized by the need of the application, such as one suitable for use in microwave oven with superior linearity of sensing properties. For example, a polymer-type humidity sensor device 200 according to the present invention may have a resistance range from 500 kΩ to 2 MΩ, resulting from the composition comprising a rubber (NBR-Acrylonitrile Butadiene Rubber) and carbon. For a specific use such as a microwave oven; a polymer-type humidity sensor 200 is characterized in that the composition comprises carbon in an amount of 15–20%±5% by volume of the polymer structure.

By using rubber, adherence between contact terminals is improved, oxidation of the terminals prevented, and an improvement is brought about in long-term stability and durability of a humidity sensor. In addition, it is possible to remove the dew point. For example, by using a natural rubber, dew on a surface of the natural rubber is absorbed by the porous natural rubber. It is also possible to produce the humidity sensor with reliability, at a small size, and at low cost.

By using carbon, as a conductive additive it is possible to stabilize the humidity detection properties under conditions of changing humidity and temperature. Furthermore, carbon increases the conductivity of the rubber and is easy to use to set impedance, current and voltage values for the interchangeability needed for the mechanical and electronical junctions. Also, it is easy to set material resistance according to designed geometrical figures. That is, it is easy to change the impedance of the material.

In addition, unlike polymeric materials used in conventional humidity sensor 4, a conductive polymer of the present invention provides a polymer-type humidity sensor 200 with fast response speed, low hysteresis, and a longer lifespan. Furthermore, unlike the conventional polymeric materials, the conductive polymer of the present invention is stable upon exposure to high temperature and high relative humidity.

Fabricated by the technology of dispersing electro-conductive particles over a polymeric material, the polymer-type humidity sensor of the present invention adopts carbon to natural rubber to maintain the resistance constant, thereby changing resistance with ease according to the geometrical figures.

Because the moisture sensing principle of the polymer-type humidity sensor of the present invention depends on the physical adsorption of moisture molecules to the sensor membrane via pores present in the surface of the membrane, the properties of the humidity sensor can be determined by the properties of the material itself as well as by the microscopic structures such as pore sizes, pore distribution, and porosity. Therefore, the polymer-type humidity sensor of the present invention produces errors within an allowable range and shows reliable operational characteristics.

Although a few embodiments of the present invention have been shown and described, it will be appreciated by those skilled in the art that changes may be made in these embodiments without departing from the principles and spirit of the invention, the scope of which is defined in the appended claims and their equivalents.

What is claimed is:

1. A polymer-type humidity sensor comprising:
    a polymer structure of a predetermined shape, wherein said polymer structure comprises a rubber and carbon; and
    a pair of electric terminals contacting said polymer structure to measure an impedance to determine a relative humidity,
    wherein the carbon added to said polymer structure is in a range of 15–20%±5% volume.

2. The polymer-type humidity sensor of claim 1, wherein the polymer-type humidity sensor has a resistance in a range of 500 kΩ–2 MΩ.

3. The polymer-type humidity sensor of claim 1, wherein the polymer-type humidity sensor has an impedance of $2 \times 10^6$Ω and $5 \times 10^5$Ω at a relative humidity range of 0% and 100% and undergoes impedance change as a function of relative humidity over the whole relative humidity range.

4. The polymer-type humidity sensor of claim 1, wherein the rubber is NBR-Acrylonitrile Butadiene Rubber.

5. The polymer-type humidity sensor of claim 1, wherein the polymer-type humidity sensor has a resistance in a range of 500 k$\Omega$–2 M$\Omega$.

6. The polymer-type humidity sensor of claim 5, wherein the polymer-type humidity sensor has an impedance of $2\times10^8\Omega$ and $5\times10^5\Omega$ at a relative humidity range of 0% and 100% and undergoes an impedance change as a function of relative humidity over the whole relative humidity range.

7. The polymer-type humidity sensor of claim 6, wherein said electric terminals are situated within said polymer structure at predetermined locations and extend outward from said polymer structure.

8. The polymer-type humidity sensor of claim 6, wherein said electric terminals are situated externally and contact outer portions of said polymer structure.

9. The polymer-type humidity sensor of claim 6, wherein the predetermined shape includes a planar surface to contact a gas having humidity.

10. The polymer-type humidity sensor of claim 6, wherein the predetermined shape includes a rounded surface to contact a gas having humidity.

11. The polymer-type humidity sensor of claim 10, wherein the predetermined shape is a cylindrical shape having said electrical terminals at opposing ends.

12. The polymer-type humidity sensor of claim 10, wherein the predetermined shape is a coil shape having said electrical terminals at edges of the coil shape.

13. A polymer structure to act as a sensing structure of a polymer-type humidity sensor, comprising:

a rubber; and carbon mixed in said rubber, wherein the sensor measures an impedance of the polymer structure to determine a relative humidity, and wherein an amount of said carbon added to the polymer structure is in a range of 15–20%±5% by volume of the polymer structure.

14. The polymer structure of claim 13, wherein the rubber is NBR-Acrylonitrile Butadiene Rubber.

15. The polymer structure of claim 13, wherein the polymer-type humidity sensor has a resistance in a range of 500 k$\Omega$–2 M$\Omega$.

16. The polymer structure of claim 15, wherein the polymer-type humidity sensor has an impedance of $2\times10^6\Omega$ and $5\times10^5\Omega$ at a relative humidity range of 0% and 100% and undergoes an impedance change as a function of relative humidity over the whole relative humidity range.

17. A microwave oven to cook food comprising:

a body including a cooking cavity;

a heating element to cook the food in the cooking cavity;

an air outlet unit to discharge air from the cooking cavity;

a control unit which controls the cooking of the food; and a polymer-type humidity sensor disposed at said air outlet to obtain information on a humidity content of the discharged air for use by said control unit, wherein said polymer-type humidity sensor comprises a polymer structure of a predetermined shape and having a rubber and carbon, and a pair of electric terminals contacting the polymer structure to measure an impedance to determine a relative humidity, wherein an amount of said carbon added to the polymer structure is in a range of 15–20%±5% by volume of the polymer structure.

18. The microwave oven of claim 17, further comprising a cooling fan which draws atmospheric air into the cooking cavity while cooling said heating element.

19. The microwave oven of claim 17, wherein the polymer-type humidity sensor has a resistance in a range of 500 k$\Omega$–2 M$\Omega$.

20. The microwave oven of claim 19, wherein the polymer-type humidity sensor has an impedance of $2\times10^6\Omega$ and $5\times10^5\Omega$ at a relative humidity range of 0% and 100% and undergoes an impedance change as a function of relative humidity over the whole relative humidity range.

21. The microwave oven of claim 20, wherein the rubber is NBR-Acrylonitrile Butadiene Rubber.

22. A polymer type-humidity sensor comprising:

a polymer structure having opposing ends, wherein said polymer structure comprises a rubber and carbon; and electric terminals, each contacting a corresponding one of the opposing ends of said polymer structure to measure an impedance to determine a relative humidity wherein an amount of said carbon added to the polymer structure is in a range of 15–20%±5% by volume of the polymer structure.

23. The polymer type-humidity sensor of claim 22, wherein said polymer structure is a cylindrical shape having said electrical terminals at the opposing ends of the cylindrical shape.

24. The polymer type-humidity sensor of claim 22, wherein said polymer structure comprises a prismatic shape having said electrical terminals at the opposing ends of the prismatic shape.

25. The polymer type-humidity sensor of claim 24, wherein the prismatic shape has a rectangular cross-section.

26. A polymer-type humidity sensor comprising:

a polymer structure of a predetermined shape, wherein said polymer structure comprises a rubber and carbon; and a pair of electric terminals contacting said polymer structure to measure an impedance to determine a relative humidity, wherein the polymer-type humidity sensor has an impedance of $2\times10^6\Omega$ and $5\times10^5\Omega$ at a relative humidity range of 0% and 100% and undergoes impedance change as a function of relative humidity over the whole relative humidity range.

* * * * *

UNITED STATES PATENT AND TRADEMARK OFFICE
CERTIFICATE OF CORRECTION

PATENT NO. : 6,806,722 B2
DATED : October 19, 2004
INVENTOR(S) : Jong-Chull Shoh et al.

It is certified that error appears in the above-identified patent and that said Letters Patent is hereby corrected as shown below:

Column 7,
Line 8, change "$2 \times 10^8$" to -- $2 \times 10^6$ --

Signed and Sealed this

Third Day of May, 2005

JON W. DUDAS
*Director of the United States Patent and Trademark Office*